United States Patent
Fahy

(10) Patent No.: US 11,659,835 B2
(45) Date of Patent: May 30, 2023

(54) METHOD OF INTRODUCTION AND REMOVAL OF HIGH CONCENTRATIONS OF CRYOPROTECTANTS BY VASCULAR PERFUSION

(71) Applicant: 21ST CENTURY MEDICINE, INC., Fontana, CA (US)

(72) Inventor: Gregory Michael Fahy, Norco, CA (US)

(73) Assignee: 21st Century Medicine, Inc., Fontana, CA (US)

(*) Notice: Subject to any disclaimer, the term of this patent is extended or adjusted under 35 U.S.C. 154(b) by 642 days.

(21) Appl. No.: 15/329,410

(22) PCT Filed: Jul. 28, 2015

(86) PCT No.: PCT/US2015/042424
§ 371 (c)(1),
(2) Date: Jan. 26, 2017

(87) PCT Pub. No.: WO2016/018890
PCT Pub. Date: Feb. 4, 2016

(65) Prior Publication Data
US 2018/0014823 A1    Jan. 18, 2018

Related U.S. Application Data

(60) Provisional application No. 62/030,205, filed on Jul. 29, 2014.

(51) Int. Cl.
*A01N 1/00* (2006.01)
*A01N 1/02* (2006.01)
(Continued)

(52) U.S. Cl.
CPC .......... *A01N 1/0247* (2013.01); *A01N 1/021* (2013.01); *A01N 1/0226* (2013.01);
(Continued)

(58) Field of Classification Search
CPC ...... A01N 1/027; A01N 1/021; A01N 1/0226; A01N 1/0284; A01N 1/0289; A61M 5/14;
(Continued)

(56) References Cited

U.S. PATENT DOCUMENTS 5,338,662 A    8/1994  Sadri
6,492,103 B1   12/2002 Taylor
(Continued)

FOREIGN PATENT DOCUMENTS

WO    02/32225 A2    4/2002

OTHER PUBLICATIONS

Fahy et al. Cryopreservation of organs by vitrification: perspectives and recent advances. Cryobiology; 48 (2004), pp. 157-178.*
(Continued)

*Primary Examiner* — Benjamin R Whatley
(74) *Attorney, Agent, or Firm* — Arrigo, Lee, Guttman & Mouta-Bellum, LLP

(57) ABSTRACT

This invention relates to the preservation of vascularized tissues and organs by freezing or by vitrification; to organ and tissue cryopreservation or banking; and to tissue and organ perfusion with cryoprotective agents (also known as cryoprotectants).

4 Claims, 6 Drawing Sheets

(51) Int. Cl.
  *A61M 5/36*    (2006.01)
  *A61M 5/142*   (2006.01)
  *A61M 5/14*    (2006.01)
  *A61M 5/44*    (2006.01)
  *A61M 5/168*   (2006.01)

(52) U.S. Cl.
  CPC ......... *A01N 1/0284* (2013.01); *A01N 1/0289* (2013.01); *A61M 5/14* (2013.01); *A61M 5/142* (2013.01); *A61M 5/36* (2013.01); *A61M 5/44* (2013.01); *A61M 5/16804* (2013.01); *A61M 5/16827* (2013.01); *A61M 2205/3331* (2013.01); *A61M 2205/3368* (2013.01)

(58) Field of Classification Search
  CPC .......... A61M 5/142; A61M 5/36; A61M 5/44; A61M 5/16804; A61M 5/16827; A61M 2205/3331; A61M 2205/3368
  See application file for complete search history.

(56) References Cited

U.S. PATENT DOCUMENTS

| | | |
|---|---|---|
| 8,679,735 B2 | 3/2014 | Fahy et al. |
| 2001/0031459 A1 | 10/2001 | Fahy et al. |
| 2007/0190517 A1* | 8/2007 | Fahy .................... A01N 1/0221 435/1.1 |
| 2010/0028850 A1 | 2/2010 | Brassil |
| 2013/0109006 A1 | 5/2013 | Owen et al. |
| 2013/0177899 A1 | 7/2013 | Taylor et al. |
| 2014/0011182 A1 | 1/2014 | Van et al. |

OTHER PUBLICATIONS

Physical and biological aspects of renal vitrification. Organogenesis 5:3 (2009), pp. 167-175.*
International Search Report from the United States Patent Office for International Application No. PCT/US2015/042424, dated Oct. 28, 2015.
Written Opinion of the International Searching Authority from the United States Patent Office for International Application No. PCT/US2015/042424, dated Oct. 28, 2015.
Baudot et al. "Towards Whole Sheep Ovary Cryopreservation," Cryobiology, 55(3), pp. 236-248, Academia Press Inc., Nov. 22, 2007.
Extended European Search Report dated Mar. 15, 2018 in EP Application No. 15828048.7.
Office Action dated Feb. 18, 2019 in EP Application No. 15828048.7.
Summons To Attend Oral Proceedings Pursuant To Rule 115(1) EPC dated Nov. 3, 2020 in EP Application No. 15828048.7.
English Translation and Original of Office Action dated Mar. 4, 2020 in Chinese Counterpart application No. 201580051464.8.
Abazari et al., "Engineered Trehalose Permeable to Mammalian Cells", PLOS One, 10(6), Jun. 26, 2015, 16 pages.
Fahy et al., "Cryopreservation of Organs by Vitrification: Perspectives and Recent Advances", Cryobiology 48, Feb. 18, 2004, 157-178.
Fahy et al., "Physical and Biological Aspects of Renal Vitrification", Organogenesis, 5(3), Jul. 1, 2009, 167-175.
Karow, A. M., "Cryoprotectants—A New Class of Drugs", J. Pharm. Pharmacol., 21(4), Apr. 1969, 209-223.

* cited by examiner

METHOD OF INTRODUCTION AND REMOVAL OF HIGH CONCENTRATIONS OF CRYOPROTECTANTS BY VASCULAR PERFUSION

CROSS-REFERENCE TO RELATED APPLICATIONS

This application claims the benefit of U.S. Provisional Application No. 62/030,205, filed Jul. 29, 2014, the entire contents of which are incorporated herein by reference.

FIELD OF THE INVENTION

This invention relates to the preservation of vascularized tissues and organs by freezing or by vitrification. It relates to organ and tissue cryopreservation or banking. It also relates to tissue and organ perfusion with cryoprotective agents (also known as cryoprotectants). The present invention is an improvement over previously known methods of cryoprotectant addition and removal for tissues, organs, and even whole organisms.

BACKGROUND OF THE INVENTION

The present disclosure relates to a method of introduction and removal of high concentrations of cryoprotectants by vascular perfusion. For example, Fahy et al., 2009 have enabled a rabbit kidney to be vitrified and transplanted with life support, but this accomplishment was limited by inadequate protection against ice formation in the renal medulla. In one aspect, the present application addresses this and other deficiencies in vascular perfusion of cryoprotectants.

In general, the introduction of vitrifiable concentrations of cryoprotectants by vascular perfusion is limited by increasing viscosity as concentrations rise. Stepwise elevation of perfusion pressure to achieve more flow (Fahy et al., 2009; U.S. Pat. No. 8,679,735 B2) has been associated with increased damage in rabbit kidneys, has been thought to increase the risk of counterproductive fluid transfer from the vascular bed to the interstitial fluid, has shown variable/inconsistent results with respect to the efficacy of equilibration with cryoprotectants, and has been done in an arbitrary way. The present application addresses these methodological and theoretical problems.

Sadri described a perfusion device that could allow for constant pressure or constant flow perfusion of organs under physiological conditions (U.S. Pat. No. 5,338,662 A). Sadri described no application of this system to problems of tissue or organ perfusion with cryoprotectants, however, and did not address any of the processes or problems described herein. The present application is not for a device but is for a method unrelated to normal physiological perfusion.

SUMMARY OF THE INVENTION

The disclosure is directed to a method of perfusion (herein called the FlowLock method) that is specifically tailored to the distribution of cryoprotectant, and especially of vitrifiable concentrations of cryoprotectant, through the vascular system in such a way that equilibration of tissue with cryoprotectants is accelerated while minimizing damage to each perfused biological system as a biological "individual," enabling a standard protocol to be followed that can accommodate biological systems with differing vascular resistances. The method is intended to address the problem of perfusing high viscosity aqueous perfusates containing cryoprotectants without excessive delays in equilibrating those cryoprotectants between the arterial perfusate and the perfused tissue or organ or organ system or organism without damage to the perfused tissue, organ, organ system, or organism. At the same time, the method is intended to provide a way of controlling arterial pressure both during the addition and the removal of cryoprotectants.

In one embodiment, the methods of the present disclosure may be characterized as being a method for equilibrating biological systems (tissues, organs, organ systems, or organisms) with cryoprotective agents by vascular perfusion, comprising:

a) Setting (designating) a lower limit to the arterial flow rate for the perfusion process;

b) Increasing the concentration of cryoprotectant in the arterial perfusate at a constant first arterial perfusion pressure until the rising viscosity of the perfusate causes the arterial flow rate to decline to become equal to the said set lower limit to the arterial flow rate of step a);

c) Holding the arterial flow rate constant at the set lower limit of arterial flow rate of step a);

d) Allowing arterial perfusion pressure to rise from the first arterial perfusion pressure of step b) to a higher pressure equal to or below a preset maximum arterial perfusion pressure as a result of rising perfusate viscosity in combination with the constant lower limit of arterial flow rate of steps a) and c); and then e) Either
  i. continuing to perfuse the biological system at the set lower limit of arterial flow of step a) above, if the arterial perfusion pressure does not reach the preset maximum arterial perfusion pressure of step d) above, or,
  ii. if the arterial perfusion pressure reaches the preset maximum arterial perfusion pressure of step d) above, allowing arterial flow rate to fall to below the set lower limit of arterial flow of step a) above as may be required to maintain the arterial perfusion pressure at the preset maximum arterial perfusion pressure of step d).

Process for Addition and Removal of Cryoprotectant

In another embodiment, the disclosure also provides an improved method for equilibrating biological systems (tissues, organs, organ systems, or organisms) with cryoprotective agents by vascular perfusion and then washing out the cryoprotective agents, comprising the steps a)-e) described above for adding cryoprotectant followed by:

f) reducing the viscosity of the arterial perfusate by beginning to raise the temperature of the arterial perfusate or by lowering the cryoprotectant concentration of the arterial perfusate, or both, while perfusing the biological system, and then;

g) if the arterial perfusion pressure is below the preset maximum value of step d) above, continuing to perfuse the biological system at the set lower limit of arterial flow rate of step a) above until arterial pressure falls to the first arterial perfusion pressure of step b) above, and thereafter maintaining the arterial perfusion pressure at the first arterial perfusion pressure of step b) above by increasing the arterial flow rate as required to do this; or h) if the arterial perfusion pressure is equal to the preset maximum arterial perfusion pressure of step d) above, increasing arterial flow as needed to maintain this pressure until such time as the arterial flow rate becomes equal to the set lower limit of arterial flow of step a) above and then holding the arterial flow rate constant at the set lower limit of arterial flow of step a) above until the arterial perfusion pressure falls to become equal to the first arterial perfusion pressure of step b) above, and thereafter maintaining the arterial perfusion pressure at the first arterial perfusion pressure of step b) above by increasing the arterial flow rate as required to do this.

Improved Process for Addition and Enhanced Safety of Removal of Cryoprotectant

In another embodiment, the disclosure also provides an improved method for equilibrating biological systems (tissues, organs, organ systems, or organisms) with cryoprotective agents by vascular perfusion and then removing said cryoprotective agents with enhanced safety, comprising all of the steps a)-e) above of the process described for adding cryoprotectants followed by:

f) reducing the viscosity of the arterial perfusate by beginning to raise the temperature of the arterial perfusate or by lowering the concentration of cryoprotectant in the arterial perfusate, or both, while perfusing the biological system, and then g) if the arterial perfusion pressure at the end of step e) above is higher than a predetermined second maximum arterial perfusion pressure lower than the preset maximum perfusion pressure of step d) above but higher than the first arterial perfusion pressure of step b) above, then, perfusing the biological system at an arterial flow rate sufficient to establish the said predetermined second maximum arterial perfusion pressure, provided that said arterial flow rate sufficient to establish the said predetermined second maximum arterial perfusion pressure does not exceed the set minimum arterial perfusion rate of step a) above;

h) as the viscosity of the arterial perfusate is lowered by beginning to raise the temperature of the arterial perfusate or by lowering the cryoprotectant concentration of the arterial perfusate, or both, while perfusing the biological system, increasing the arterial flow rate so as to maintain the arterial perfusion pressure at the said predetermined second maximum arterial perfusion pressure;

i) holding the arterial flow rate constant when the arterial flow rate becomes equal to the pre-set minimum arterial flow rate of step a) above, until the arterial perfusion pressure becomes equal to the first arterial perfusion pressure of step b) above; and then j) raising the arterial perfusion pressure as needed to maintain the first arterial perfusion pressure of step b) above.

Improved Process for Addition and Accelerated Removal of Cryoprotectant

In another embodiment, the disclosure also provides an improved method for equilibrating biological systems (tissues, organs, organ systems, or organisms) with cryoprotective agents by vascular perfusion and then rapidly removing said cryoprotectant, comprising all of the steps a)-e) above of the process described for adding cryoprotectants followed by:

f) reducing the viscosity of the arterial perfusate by beginning to raise the temperature of the arterial perfusate or by lowering the cryoprotectant concentration of the arterial perfusate, or both, while perfusing the biological system, and at the same time, g) maintaining the arterial perfusion pressure that is present at the end of step e) above for a time longer than the time required for the arterial flow rate to increase to equal or exceed the minimum set arterial flow rate of step a) above; and then h) locking the arterial flow rate at the rate present at the end of the said time longer than the time required for the arterial flow rate to increase to equal or exceed the minimum arterial flow rate of step a) above until the arterial perfusion pressure declines to the first arterial perfusion pressure of step b) above; and then i) locking the arterial pressure at the first arterial perfusion pressure of step b) above by increasing the arterial flow rate as necessary to maintain that arterial perfusion pressure.

DETAILED DESCRIPTION OF THE INVENTION

In one embodiment, the disclosed method can be used to control arterial perfusion pressure both during the introduction and the removal of high viscosity cryoprotectant solutions, such as solutions whose total concentrations equal or exceed 4 molar or whose viscosities equal or exceed about 1.25-1.5 cP (centipoise). In one embodiment, the disclosed method can be used to facilitate equilibration during both a period of increasing viscosity and a period of decreasing viscosity, for example during elevation of permeating cryoprotectant concentrations above 4M and during reduction of permeating cryoprotectant concentrations from above 4M to a final value near or equaling 4M.

Figure 2:
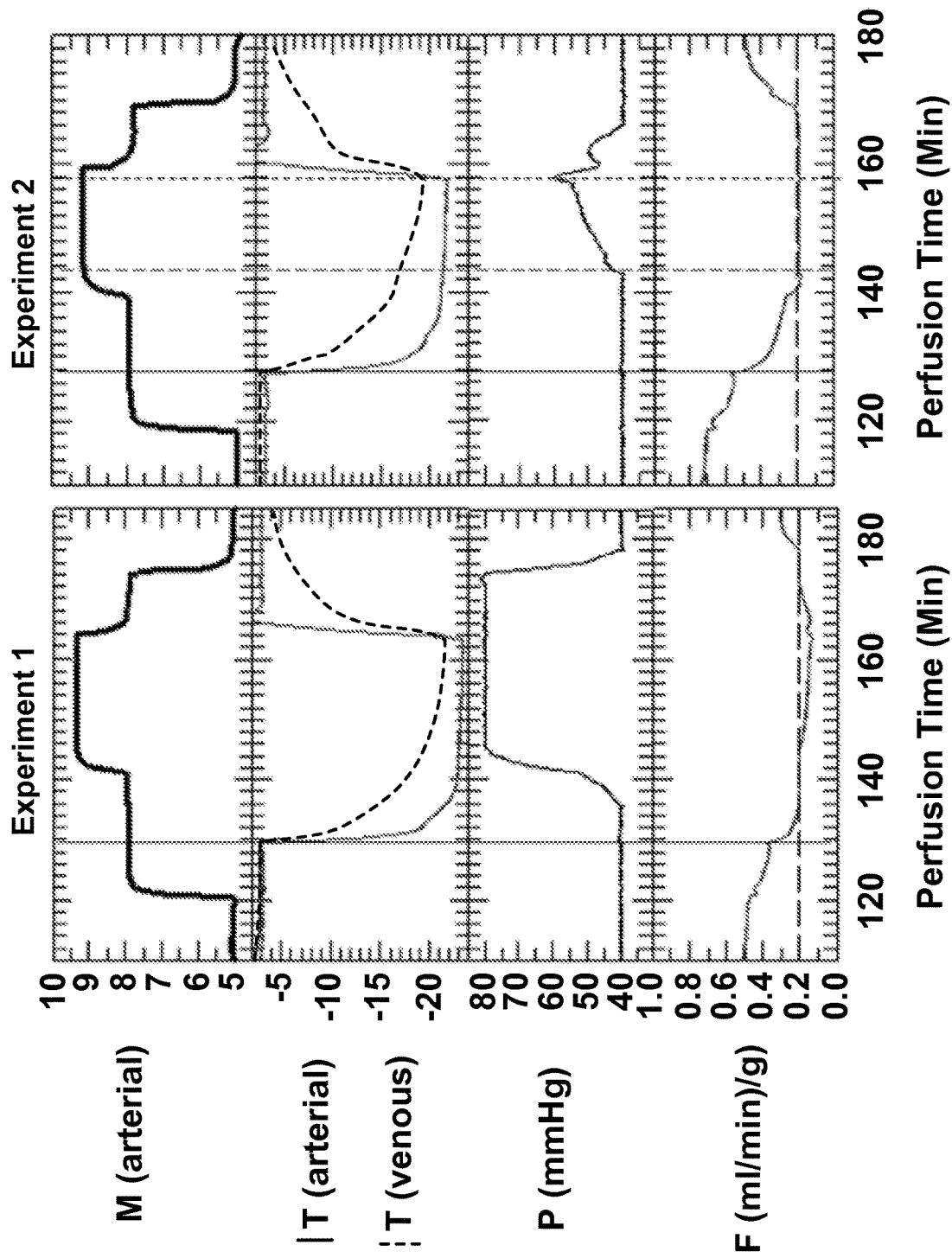
FIG. 2 illustrates the principle of the FlowLock method as applied to rabbit kidneys.

In one embodiment summarizing the method disclosed herein, the method as it relates to the addition of cryoprotectant to a perfused system comprises a) locking arterial flow at a minimum level as viscosity increases and allowing arterial pressure to rise as a result to a pressure of not more than a pre-set maximum, and b) holding arterial pressure at the elevated level of not more than the pre-set maximum until cryoprotectant addition is completed, during which time arterial flow is allowed, if necessary to avoid exceeding the pre-set maximum arterial pressure, to decline to below the nominal minimum arterial flow, the actual flow being determined by the vascular resistance of the perfused biological system and the prevailing viscosity (as illustrated below in the left side of FIG. 2, see discussion below).

In one embodiment, this method is useful for a number of purposes. For example, and without limitation, first, it allows the natural vascular resistance of individual perfused systems to dictate the arterial perfusion pressure needed to equilibrate said systems with the perfused solutes, rather than arbitrarily imposing higher than necessary pressures that may be damaging. Second, in the case of kidneys specifically, it allows the kidney to determine which pathway is emphasized for equilibration, i.e., either the vascular route (if vascular resistance is low, enabling even inner medullary cryoprotectant equilibration to be achieved via vascular perfusion) or the glomerular filtration route (which, if vascular resistance is higher and perfusion pressures are therefore higher, may deliver more cryoprotectant to the inner medulla than will perfusion of the vasa recta). Third, the method has diagnostic applications involving understanding the balance between fluid/cryoprotectant extravasation due to elevated pressures and fluid retention in the vascular system due to elevated perfusate viscosity. The method is not a method for overcoming vascular obstructions such as emboli by using high perfusion pressures.

In one embodiment, the method as it relates to the removal of cryoprotectant from the biological system comprises the additional steps of c) reducing the arterial concentration of cryoprotectant or other viscous water soluble solute while holding arterial perfusion pressure constant at the pre-set maximum, during which time the arterial flow will rise as viscosity falls, d) locking arterial flow at the previous flow minimum when that flow minimum has been reached, which then causes the arterial pressure to fall below the pre-set maximum as viscosity continues to fall, and finally e) when the arterial pressure falls to a safe level deemed appropriate for the resumption of constant pressure perfusion, the arterial pressure is held constant, after which arterial flow will rise according to the reduction in effective vascular resistance caused by further declines in perfusate viscosity and other factors. Certain variations on this basic method are also described herein to handle more specific requirements of given organs.

These novel and previously-unexplored perfusion techniques have for the first time enabled perfused biological systems to be better equilibrated with cryoprotectants and, in the case of one exemplary system, the rabbit kidney, to retain high levels of viability as verified by transplantation and life support by the transplanted system despite much more thorough equilibration than has been achievable with previously known (U.S. Pat. No. 8,679,735 B2) methods. These results for the first time even enable rabbit kidneys to be equilibrated with sufficient cryoprotectant to escape from damaging levels of devitrification (ice formation) during rewarming from the vitreous or near-vitreous state while retaining full life support capacity after transplantation. The overall method, referred to as the "FlowLock" Method, therefore brings the problem of organ cryopreservation in general considerably closer to a successful outcome.

In the current context, the term "vitrifiable" indicates that a solution or living system can be vitrified at cooling rates that are applicable to perfused tissues and organs, i.e., at a cooling rate of 20° C./min or less, and more preferably at a cooling rate of 5° C./min or less. In the current context, "solutions" are always aqueous solutions. Cryoprotectants are also called cryoprotective agents, or CPAs, and the words "cryoprotectant" and "cryoprotective agents" or "cryoprotective agent" are used interchangeably. The nature of cryoprotectants is well known in the art, and the National Library of Medicine has a specific subject category for "Cryoprotective Agents," which is incorporated herein by reference in its entirety. By way of example, "cryoprotectants" can include both permeating cryoprotectants (pCPA) (typically, having molecular masses less than 100 daltons and being able to enter cells at useful rates, specific examples being dimethyl sulfoxide, ethylene glycol, formamide, glycerol, propylene glycol, etc. (see also Karow, 1969, for a more complete listing), but which may also include newer molecules such as multiply acetylated trehalose, whose permeability properties have been altered to enable this normally impermeant molecule to enter the cell at useful rates (see Abazari et al., 2015) and non-permeating CPAs (npCPA, consisting of cryoprotectants with molecular masses greater than 100 daltons that do not pass through cell membranes at appreciable rates under their conditions of use). The term "cryoprotectant" as used herein may refer to one or to multiple cryoprotectants, and to either pCPA alone or to a mixture of pCPA and npCPA. "Urine" in the present context refers to the fluid that emerges from the ureter during cryoprotectant perfusion, which is an ultrafiltrate of the cryoprotectant solution and bears no resemblance to ordinary urine either conceptually or in composition.

No specific cryoprotectant solutions are required to practice the method of the disclosure as described, the method being applicable to, for example, the use of any sufficiently non-toxic cryoprotectant solutions. However, several examples are provided herein and in the cited references, and these examples in combination with general skill in the art are sufficient to enable the processes described herein to be practiced with success. Specific embodiments of the disclosure as described in detail above are now illustrated by means of and discussed in connection with particular Examples.

Example 1: FlowLock Method for Cryoprotectant Loading Only

Figure 1:
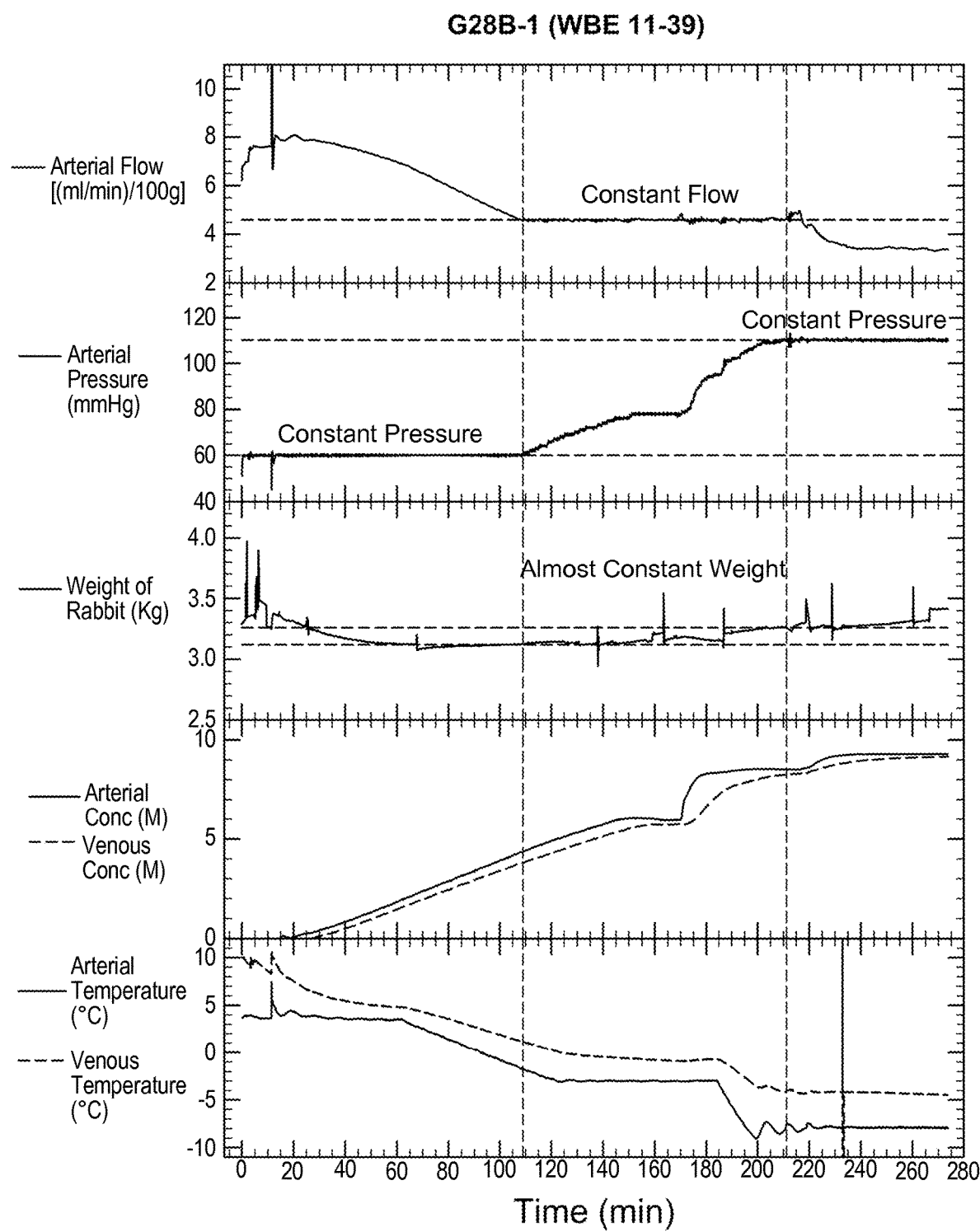
FIG. 1 illustrates the application of the principle of the FlowLock method of adding cryoprotectant in the case of a whole rabbit.

The FlowLock method for cryoprotectant addition to a perfused biological system is illustrated in FIG. 1. A New Zealand White Rabbit was perfused at an arterial pressure of 60 mmHg while the M22 vitrification solution (described in Fahy et al., 2004 and U.S. Pat. No. 8,679,735 B2) was gradually introduced. The top panel shows that, as the cryoprotectant concentration increased (shown in the fourth panel from the top), arterial flow decreased as a result of the increasing viscosity of the cryoprotectant solution. However, when the arterial concentration reached 4M, the arterial flow was "locked" at the then-prevailing value. This caused the arterial pressure to increase from 60 mmHg to, ultimately, 110 mmHg (second panel from the top), and yet, despite this 83% increase in pressure, the rabbit weight increased by less than 7%.

While not wishing to be bound by any theory, the idea behind this protocol was that the same viscosity increase that raises vascular resistance would also slow transudation of vascular fluid from the vasculature to the interstitium, making it unnecessary to curtail flow to compensate for increased viscosity. The failure of the rabbit to gain appreciable weight during the period of clamped or "locked" flow supports this conjecture and validates the method. Furthermore, because the rabbit consists of a vast number of different organs and tissue systems, the experiment provides support for the applicability of the FlowLock method to all perfused organs and tissues as well as to multi-organ systems and whole organisms.

The FlowLock cryoprotectant addition ("loading") method has a number of advantages in addition to maintaining flow and thus maintaining the delivery of cryoprotectant to a perfused biological system. First, it enables the perfused system rather than the method user to determine the pressure increase profile that takes place: this is simply the result of the intrinsic apparent vascular resistance (vascular resistance uncorrected for viscosity) of the perfused biological system, which means that the pressure profile is individualized based on intrinsic differences from system to system. This removes the need to guess at an arbitrarily imagined ideal pressure or series of pressures and to guess at appropriate timing for step changes in pressure. In addition, the FlowLock method changes pressure in a smooth and continuous fashion, whereas previously known methods employed abrupt changes in pressure that may be unnecessarily stressful to delicate vascular structures, particularly at low temperatures as illustrated in the lowest panel of FIG. 1 and in even more extreme examples given in Fahy et al. 2004 and Fahy et al. 2009, in which organs are perfused at temperatures as cold as about −22° C., at which temperatures tissues and cells may be brittle and easily damaged by mechanical stresses such as abrupt stretching.

Since the rate limiting factor for cryoprotectant distribution into perfused organs or tissues may often be the flow rate of the arterial supply of cryoprotectant into the specific organ or tissue of interest, the ability to select a flow rate that has been previously determined to be safe for that system and to maintain it throughout much or all of the process of cryoprotectant introduction helps to overcome a major obstacle to cryoprotecting tissues or organs by vascular perfusion. In addition, the ability to select an upper limit for pressure excursion allows damage caused by the FlowLock method to be easily controlled and investigated. Rather than having to analyze the effects of a more complex protocol, the upper pressure limit can simply be experimentally adjusted to determine what is best for the type of system at hand.

The FlowLock method as evaluated in the whole rabbit model was found to enable the mean mass percent of ice per tissue to be as low as 0.75% w/w when 42 different organs and tissues were sampled and tested by differential scanning calorimetry for the quantity of ice that melted after previous cooling to below the glass transition temperature followed by slow rewarming (Fahy et al., unpublished results). A level of 0.75% w/w ice in a given tissue may be compatible with its survival after rewarming (Fahy et al., 2009). More than 80% of all sampled tissues showed no ice formation at all in the best FlowLock series tested in the whole-rabbit model (Fahy et al., unpublished results). This again supports the universality of applicability of the FlowLock method to all tissues and organs that may be of interest in the context of banking for therapeutic applications or experimental investigations.

Example 2: FlowLock Method for Cryoprotectant Addition and Removal

FIG. 2 shows the disparate responses of two different rabbit kidneys (Experiments 1 (left) and 2 (right)) having very dissimilar vascular resistance values prior to cryoprotectant perfusion. The fundamental perfusion protocol was as described in previously known methods (Fahy et al., 2004, 2009; U.S. Pat. No. 8,679,735 B2), but the FlowLock method was superimposed on it for both the loading (addition) and the unloading (removal) of the cryoprotectant.

In the standard method in use in our laboratory, which need not be followed to practice the FlowLock Method, cryoprotectant is added slowly to a first intermediate concentration (in this case, 5M cryoprotectant) after which there is a pause to allow time for cryoprotectant uptake at this relatively safe first intermediate concentration. The next step is to jump to a second intermediate concentration near 8M and to maintain this concentration for a sufficiently long time to enable the organ to be cooled to ~22° C. without freezing. The organ is then cooled to ~−22° C. (onset indicated in FIG. 2 by vertical lines) by lowering the temperature of the arterial perfusate, the cooling process requiring about 10 min. The next step is to jump to the final concentration (in this case, the vitrification solution known as M22, described in the cited previously known methods, whose concentration is about 9.4M) and to maintain this peak concentration for at least 20 min to render the kidney vitrifiable and sufficiently stable against ice formation during rewarming. After the M22 step, the concentration of the arterial perfusate is lowered, typically back to the same level as the second intermediate concentration, and then, after a pause, the concentration is lowered abruptly a second time, typically back to the first intermediate concentration. The figure depicts the perfusion protocol only from the stage of the first intermediate concentration during loading to the first intermediate concentration during unloading (washout) of the cryoprotectant.

In the past, this baseline protocol has been studied in combination with various step changes in pressure, especially at the moment of onset of M22 perfusion and at the moment M22 perfusion has been programmed to stop. However, it has never been studied in combination with gradual and continuous changes in perfusion pressure during either cryoprotectant addition or washout or both, it has never been studied in combination with pressure changes that were not simultaneous with the onset and end of perfusion with the peak concentration of cryoprotectant, and it has not been studied in combination with any method in which pressure was varied only as the result of holding flow constant.

The departure representing the FlowLock method as illustrated in FIG. 2 begins shortly after the onset of cooling to −22° C. As highlighted by the vertical line at the onset of cooling, cooling leads to a steep increase in viscosity and, hence, to a steep decrease in perfusate flow (lowermost panels). In the experiment shown on the left, the flow rate of the kidney at the onset of cooling to −22° C. was already low (less than 0.4 (ml/min)/gram), and cooling rapidly lowered it by a further factor of two, but at that point, further reduction in flow was prevented by a steady elevation in perfusion pressure sufficient to lock the flow rate at 0.2 (ml/min)/gram. Pressure rose smoothly and gradually to the maximum permitted value of 80 mmHg, at which point pressure was maintained constant and flow was allowed to decline to lower values. Coincident with reduction of arterial concentration and with a return from −22° C. to −3° C., perfusate viscosity decreased, resulting in a rise in flow rate at the previously-established constant pressure. Upon returning flow to the previous minimum or "locked" value, flow was again held constant to enable the arterial pressure to descend smoothly, continuously, and gradually back to the baseline safe pressure for high temperature, low viscosity perfusion of 40 mmHg. Once pressure descended to the standard 40 mmHg, it was again locked at 40 mmHg, and flow then naturally increased as perfusate viscosity further declined. Changes in pressure associated with both the loading and the unloading phase of the FlowLock Method required several minutes to be completed, in contrast to the much more rapid changes of the previously known methods, a factor which may reduce damage to the perfused organ.

The same method was also applied in the experiment depicted on the right, but in this case the flow rate of the kidney was about 50% higher at the onset of cooling to −22° C. Consequently, locking the flow at the same 0.2 (ml/min)/g value as shown on the left resulted in only a relatively small increase in perfusion pressure, which at no point approached the 80 mmHg limit of the experiment shown on the left, and this enabled the flow to be maintained at the target 0.2 (ml/min)/gram without compromise. As a result of this, the kidney whose perfusion is shown on the right had better perfusion with the highest concentration of cryoprotectant, but the kidney whose perfusion is depicted on the left was perfused far more effectively than it would have been under a constant pressure protocol, making it much more comparable to the Experiment 2 kidney on the right than it otherwise would have been, and in addition benefitted from a compensating increase in glomerular filtration which allowed it to offset to some degree the relevant consequences of its lower perfusion rate, as explained in the next paragraph. Note also that the rates of change of pressure were much lower for the kidney on the right than for the kidney on the left, illustrating that although the rates of change of pressure with the FlowLock Method will necessarily always be smaller than for the previously known abrupt step methods, they will also be dependent upon the specific perfused system. Fortunately, these rates need not be specified to practice the disclosure, since the process of the present disclosure is carried out without regard to rates of pressure change.

The limiting factor for kidney cryopreservation by vitrification is devitrification (ice formation during rewarming) in the inner medulla caused by failure to distribute cryoprotectant as efficiently to the inner medulla as to the rest of the kidney prior to vitrification. In the case of the kidney, the inner medulla receives, in vivo, about 1-2% of total renal blood flow, but it receives 100% of non-reabsorbed plasma ultrafiltrate, and in fact this plasma ultrafiltrate flows through the inner medulla three times, once through the descending limb of the loop of Henle, once through the ascending limb of the loop of Henle, and once through the collecting ducts as they descend from cortex to papilla to pelvis. Thus the kidney is an important special case in which the FlowLock method is particularly advantageous because it compensates for low perfusion rates particularly in the inner medulla, where they are the most critical, by increasing glomerular filtration and delivery of cryoprotectants to the inner medulla by elevating arterial pressure. However, it does not unnecessarily raise perfusion pressure for kidneys that tend to deliver more cryoprotectant by the direct vascular route and thus may not be in as much need of equilibration via the glomerular filtration route.

In a variation of the FlowLock method, the tissue/organ flow rate may be locked with no explicit limitation on maximum pressure. In this case, damage is prevented by locking the flow at a level that is insufficient to result in a damaging increase in pressure. This concept is illustrated in the right panel of FIG. 2, in which establishing an upper limit on pressure was immaterial. However, it may apply equally well to the case shown in the left panel of FIG. 2, in which the lack of a pressure limit would have allowed pressure to rise to well above 80 mmHg as flow was held constant, but in which the higher arterial pressure may still have been tolerable. Practicing the FlowLock method has indicated, for example, that an upper pressure limit of 90 mmHg is no more damaging than 80 mmHg, whereas in the previously known methods involving abrupt pressure changes, there was a tendency for damage to increase with pressure in a steady fashion as pressure was elevated within the range of 50-90 mmHg (Fahy, unpublished observations). In practice, there will always be some upper boundary on the safe arterial perfusion pressure, but the FlowLock method will be effective as long as the perfused tissue or organ or organ system is perfused at a pressure that is at or below this upper boundary, whether this upper boundary is known and specified or not. For safety and consistency, however, a practical upper pressure limit should preferably be set that should not be exceeded. Typically, upper pressure limits for the FlowLock method may range from about 5 mmHg to 130 mmHg, depending on the size and vascular resistance of the system in question (for example, 5-10 or 5-15 mmHg for a liver or for a lung, and 50-130 mmHg for an organism) or more generally, 10-100 mmHg.

For comparison to the previously described methods, the examples of FIG. 2 show that in neither of these two extreme cases did pressure changes coincide with the onset or with the ending of M22 (peak concentration) perfusion. In the left panel, the mismatch between the onset of pressure change and the onset and end of M22 perfusion is so extreme as to be readily apparent to the naked eye, and no highlighting of this mismatch is needed. In the right panel, the long-dashed vertical line shows that the onset of pressure change follows the onset of the computer switch to M22 by approximately 5 minutes, while the onset of pressure change associated with the reduction of viscosity (marked by the short-dashed vertical line) appropriately precedes the onset of M22 washout by about two minutes due to the prior rewarming of the kidney, with its attendant decrease in viscosity and resulting increase in perfusate flow.

In contrast, in a previous method (U.S. Pat. No. 8,679,735 B2), "pressure can be conducted at a first pressure . . . before perfusion with said vitrifiable concentration of cryoprotectant and can be raised to a second pressure . . . when perfusion with said solution begins," (col. 10, lines 16-21, emphasis added). This method differs from continuous pressure elevation resulting from locking the organ flow rate and the natural effect on pressure of the intrinsic vascular resistance of the perfused system itself independent of the onset of perfusion of a specific vitrifiable solution. Also, in describing FIG. 10 of the '735 specification, that specification notes that "the effect of arterial perfusion pressure during M22 perfusion on tissue equilibration with cryoprotectant" (col. 8, lines 4-6) was determined by the following method: "in all cases, . . . the arterial perfusion pressure was 40 mmHg prior to perfusion with M22, and pressure was set to the value plotted at the time of onset of M22 perfusion" (col. 8, lines 7-11, emphasis added) rather than being governed by the combination of a constant flow rate and the vascular resistance of the perfused kidney. Further, according to the data of Table 4 of '735 and the accompanying commentary about it in '735, perfusing at pressures above 60 mmHg was counterproductive to tissue equilibration, perhaps because of damage caused by step changes in pressure to and from pressures above 60 mmHg, whereas in the present disclosure, we observe no problem with equilibration when pressures vary between 60 and 90 mmHg, perhaps due to the more gentle method of changing pressure in the present disclosure. This represents a fundamental advance in the ability to use higher pressures to drive cryoprotectant equilibration, which is vital to the successful banking of vascularized tissues, organs, organ systems, and potentially organisms.

In the same previously known method ('735), during washout of the peak concentration of cryoprotectant, "perfusion pressure at the onset of, during, or after cryoprotectant dilution can be lowered to a pressure below that used during perfusion below −10° C.," (col. 10, lines 52-54, emphasis added) but this does not contemplate lowering pressure prior to cryoprotectant dilution as shown in the right panel of FIG. 2 and does not contemplate allowing the pressure to fall continuously and smoothly as a result of locking the flow at a constant value during washout and according to the vascular resistance of the perfused system rather than abruptly in one step to a preset pressure. There is nothing in the previously known method to suggest that pressure should be lowered by locking the perfusion rate, and in the normal art, pressure has been lowered by lowering, not locking, the arterial flow rate, resulting in abrupt pressure reduction, which may be damaging, based on tolerance of higher pressures in the present disclosure.

Only one example of the process of altering pressure is illustrated in '735, and that is in Example 6 (FIG. 11), in which it is made very clear that pressure increases and decreases are abrupt and unrelated to any use of constant flow perfusion or any effect of the vascular resistance of the perfused organ or of the viscosity of the perfusate, and that except for these abrupt step changes in pressure, pressure is always held constant. This is important for interpreting the meaning of '735 claims 7-9, 11, 29, and 33, all of which specify pressure target ranges for an abrupt switch from one pressure to another pressure in the stated range, but none of which specify gradual variation of pressure within these ranges or gradual variation of pressure within these ranges as a result of imposing constant flow conditions in the face of changing viscosities, as required by the nature of the current disclosure. Further, claims 7-9, 11, 29, and 33 are limited by the features of claim 1 of the '735 specification, and those limitations need not apply in the case of the present invention (see, for example, Example 1).

In summary, the present principle and method by which pressure changes both during cryoprotectant addition and cryoprotectant washout are effected are not contemplated by and are novel over the previously described methods.

Figure 3:
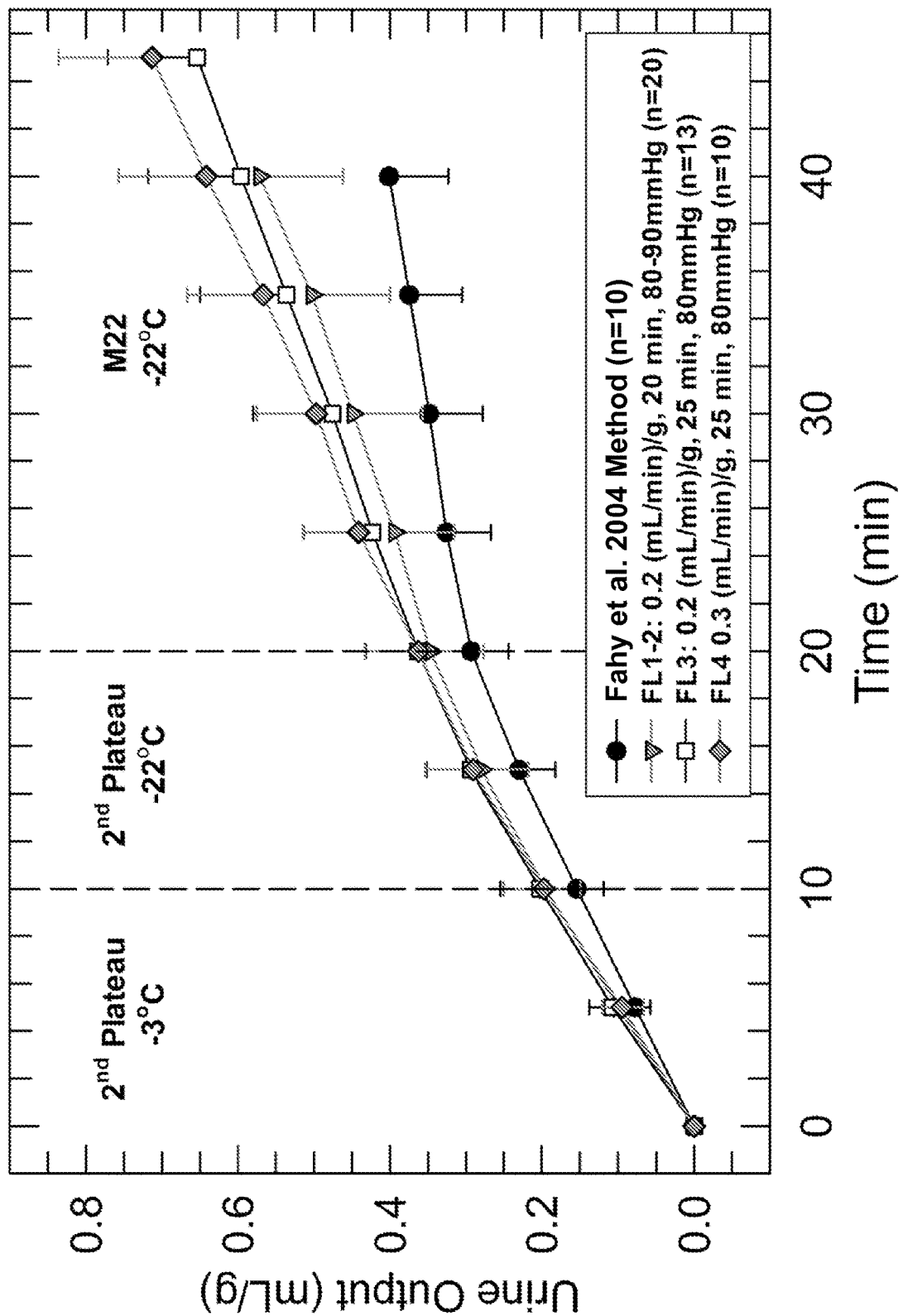
FIG. 3 illustrates the effect of the FlowLock method on urine output by rabbit kidneys.

Example 3: The FlowLock Method Improves Urine Output During Cryoprotectant Perfusion FIG. 3 shows the efficacy of the FlowLock method for increasing urine output during the perfusion of rabbit kidneys with the "M22" vitrification solution described in U.S. Pat. No. 8,679,735 B2 according to the scheme illustrated in FIG. 2. As in the standard method, the second intermediate concentration ("$2^{nd}$ plateau" concentration) was first perfused at $-3°$ C. to prepare the kidney for cooling to $-22°$ C. and was then perfused at $-22°$ C. to cool the kidney in preparation for perfusion with the peak concentration, and these phases of the perfusion are denoted in the figure and are demarcated by vertical lines.

In the standard (constant pressure) method described in Fahy et al. (2004), cumulative urine production, which was continuously retrieved by pump and diverted to a graduated cylinder for quantification each 5 min, reached about 0.3 ml/gram at the beginning of perfusion with M22 and then, owing to greater viscosity and lowered flow rates, slowed, reaching about 0.4 ml/g by the end of a standard 20 min M22 perfusion period (baseline method, 10 perfusions). By locking flow at a nominal 0.2 (ml/min)/g as illustrated in FIG. 2, urine output progressively diverged from the baseline method output through the initial $-22°$ C. perfusion period. As M22 perfusion began, the slowing of urine output seen in the previously known method was blunted, resulting in an increasing separation between the urine production seen in the FlowLock perfusions and the previously known perfusions. In FlowLock 1 (FL1), pressure was limited to a maximum of 90 mmHg, and in FlowLock 2 (FL2), pressure was limited to 80 mmHg, but several kidneys did not reach either of these limits, and there was little difference in urine production between FlowLock 1 and FlowLock 2 overall, so the results are pooled in FIG. 3. [As noted above, there was also no difference in viability between kidneys that reached 90 mmHg and those that reached 80 mmHg, as judged from post-transplant serum creatinine curves (data not shown)] The FL1-2 intervention elevated urine output at the end of M22 perfusion to about 0.6 ml/g, which is about a 50% improvement over the baseline method. The FlowLock 3 (FL3) protocol was the same as FL2 except that the M22 perfusion time was extended from 20 min to 25 min. This resulted in a further gain of about 0.05 ml/g, or another 12% improvement over baseline. Setting the flow limit to 0.3 (ml/min)/g while keeping other features of FL3 the same (the FL4 protocol) raised urine output by a further ~0.06 ml/g after 25 min of perfusion, for a total gain of about 78% over baseline.

Good survival of kidneys has been obtained after locking flow at nearly 0.5 (ml/min)/g, so the practical upper limit of locked flow in the FlowLock Method, at least as applied to the extreme case of perfusion with the intensely concentrated and very viscous (~4.34-4.83 cP at room temperature, and ~38.7 cP at $-22°$ C.) M22 solution, is about 0.3-0.5 (ml/min)/g. For use with much less concentrated and less viscous solutions, it is anticipated that locking renal flow at 0.5 (ml/min)/g, and at even higher flows, such as 0.6, 0.7, and even 0.8 (ml/min)/g, would be acceptable and efficacious.

These limits need to be put into perspective for other organs, however, since the kidney receives a disproportionate amount of the total cardiac output and has a nominal flow rate prior to cryoprotectant introduction of about 0.8-1.2 (ml/min)/gram, which is higher than for most other organs. Therefore, expressed on a percentage basis, limits of 0.1-0.8 (ml/min)/gram equate to limits of 8-100% of initial (prior to the introduction of cryoprotectant) flow or, more normally for perfusion with vitrifiable concentrations of cryoprotectant, 0.2-0.4 (ml/min)/gram equates to (0.2/1.2-0.4/0.8)× 100=16-50% of initial flow, and 0.2-0.3 (ml/min)/gram equates to 16-38% of initial flow. A good working mean percentage for most organs, including the kidney, would be 25% of initial flow, or more generally from 15 to 40% of initial flow. Thus, the FlowLock Method can be applied by using either a fixed flow rate standard for all organs as per the examples shown above or a flow rate that is a fixed percentage of the flow rate of the organ prior to perfusion with cryoprotectants. For the perfusion of resins, which are much more viscous than cryoprotectant solutions, through fixed tissue for electron microscopy, or for the perfusion of other viscous water soluble solutes, fixed flow rates in the range of 1-20% of the flow rate prior to resin or other viscous water soluble solute perfusion may be preferable, although fixed material may tolerate higher perfusion pressures.

Example 4: The FlowLock Method Increases Urine Cryoprotectant Concentration

Figure 4:
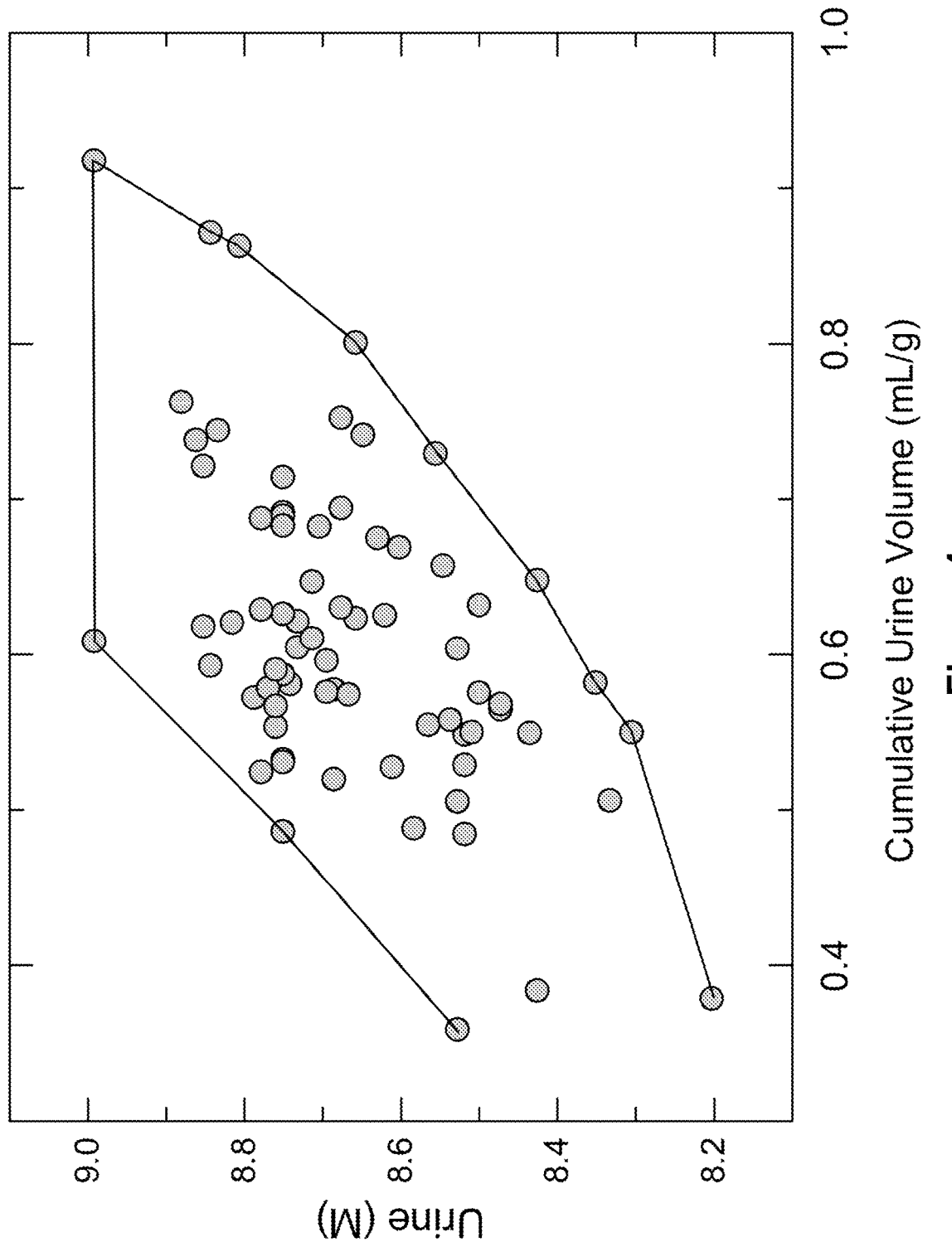
FIG. 4 illustrates the global relationship between urine output and urine concentration in the case of rabbit kidneys.

FIG. 4 shows that as urine volume increases relative to the mass of a perfused kidney, as is induced by the FlowLock Method, there is a corresponding increase in urine concentration. The drawn lines indicate that there is a response in both the poorest-equilibrating kidneys (lower line) and the best-equilibrating kidneys (upper line), kidneys in between responding in similar fashion to the kidneys on the low and high extremes. The difference between the upper and lower lines is believed to result from differing initial flow rates and vascular resistance values from kidney to kidney, i.e., from differences between kidneys in the second, competing pathway by which renal medullary equilibration can take place (vascular perfusion, which is also promoted by the FlowLock Method).

Figure 5:
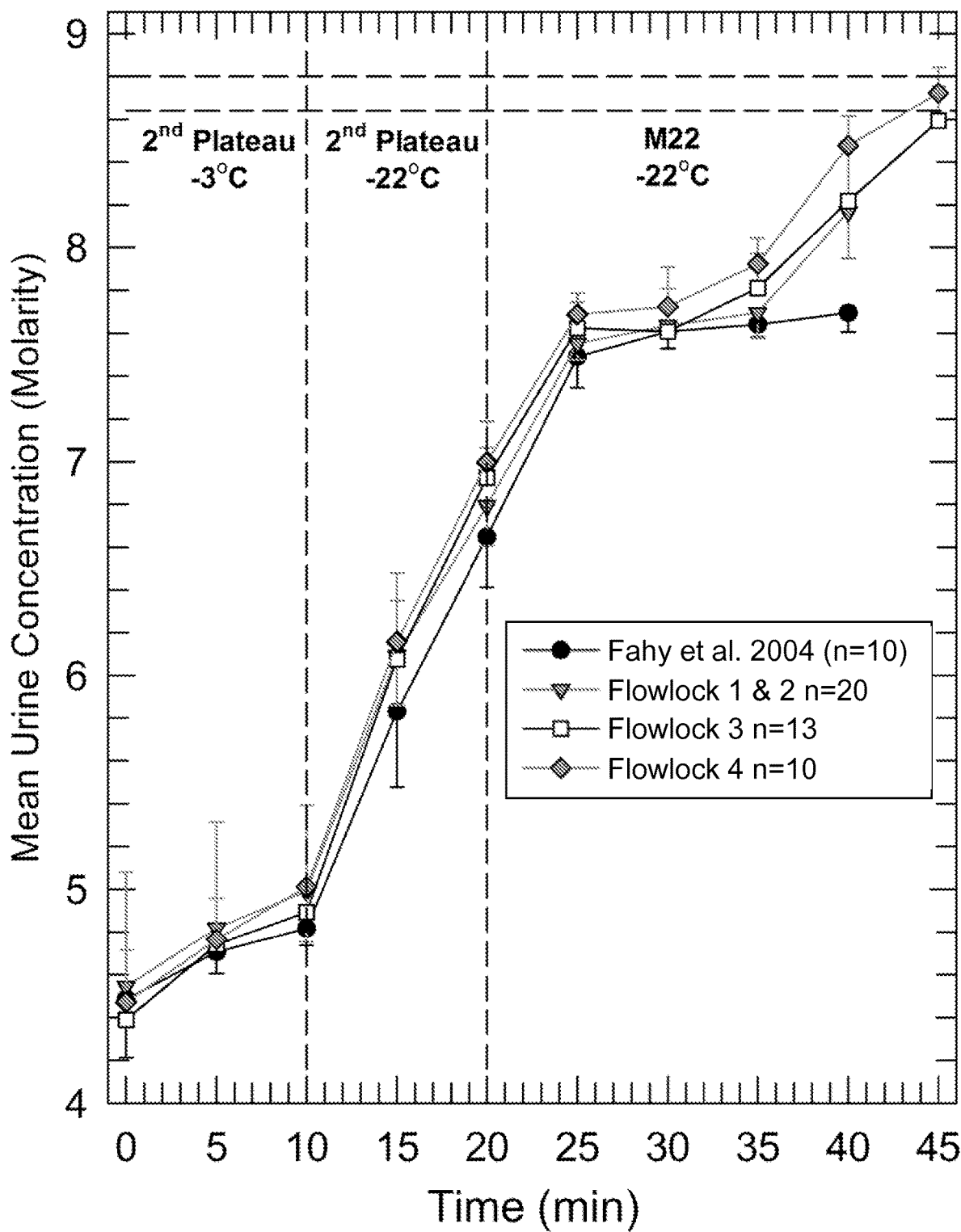
FIG. 5 illustrates the effects of specific FlowLock conditions on the concentration of cryoprotectant in the urine of rabbit kidneys.

FIG. 5 shows results in the same format as FIG. 3. The departure of the urine volume curves from those seen in the baseline (constant pressure) Fahy et al. (2004) method as depicted in FIG. 3 begins to correlate strongly with increased urine concentration only during the last 5 minutes of a 20 min M22 perfusion period. Although the effect of the locked flow on urine concentration is visible prior to this, it becomes significant and is amplified only after 15 minutes in this test system. There is almost as much gain in urine concentration between 20 and 25 min as there is between 0 and 20 min of M22 perfusion.

We interpret this result to indicate that the nephron is like a pipeline that contains a certain volume that must be displaced by new filtrate before the presence of that new filtrate can be detected at the end of the pipeline. Despite increased volume flow, the volume emerging remains dilute until the wave front of more concentrated cryoprotectant begins to emerge. Thus, by about 10 min of M22 perfusion, the displacement of the original 5M solution in the nephron by the transitional ~7.9M solution is nearing completion, but the M22 introduced into the renal artery 10 minutes previously has not yet begun to emerge from the ureter. After another 5 min, the M22 wave begins to emerge, and continues to the 25 min time point. The utility of the FlowLock Method seems to arise in part from beginning the process of "pipeline" fluid displacement sooner than in the previously known method, and in part from pushing cryoprotectant through the nephron "pipeline" more rapidly, thus allowing the wave front of more concentrated cryoprotectant to emerge from the nephron and from the ureter sooner, before limiting toxicity is experienced in the high-flow, rapid-equilibration regions of the kidney (particularly, the cortex).

A critical feature of FIG. 5 is that, for the FlowLock 3 and FlowLock 4 protocols, the final urine concentrations approach or are in the zone of 8.64-8.8M (indicated by horizontal dashed lines) or higher. The significance of this result is that kidneys whose urine concentrations reach these values can be vitrified and rewarmed without the conversion of more than 1% of their inner medullary mass into ice during rewarming from the vitrified state. Confining inner medullary ice content to less than or equal to 1% is thought to be compatible with the survival of the inner medulla and the recovery of normal renal function following transplantation. The survival of a previously vitrified and transplanted kidney using previously known technology (Fahy et al., 2009) employed a similar final pressure level of 80 mmHg during M22 perfusion, but did not achieve less than 1% ice formation in the inner medulla, and renal medullary damage was evident histologically when the kidney was examined 48 days after transplantation, presumably due to this excessive inner medullary ice formation. It is believed that the chronic impairment of renal function seen for this kidney after transplantation is also due at least in part to the prior inner medullary ice damage. Therefore, the FlowLock Method, which enables more inner medullary cryoprotectant equilibration, less ice formation after rewarming from the vitrified state (devitrification), and better retention of viability after M22 perfusion at higher pressures, represents a major technological advance over the previously known methods.

The optimal method is a tradeoff between damage from higher locked flows and higher perfusion pressures on the one hand and damage from longer exposure times on the other. For the rabbit kidney, we believe the best tradeoff is to use minimum flows of 0.1-0.25 (ml/min)/g, peak concentration perfusion durations of 20-30 min, and upper pressure limits of 70-100 mmHg. Expressed as a percentage of the pre-cryoprotectant flow rate, this flow rate range encompasses 8-31% of the pre-cryoprotectant flow rate.

Figure 6:
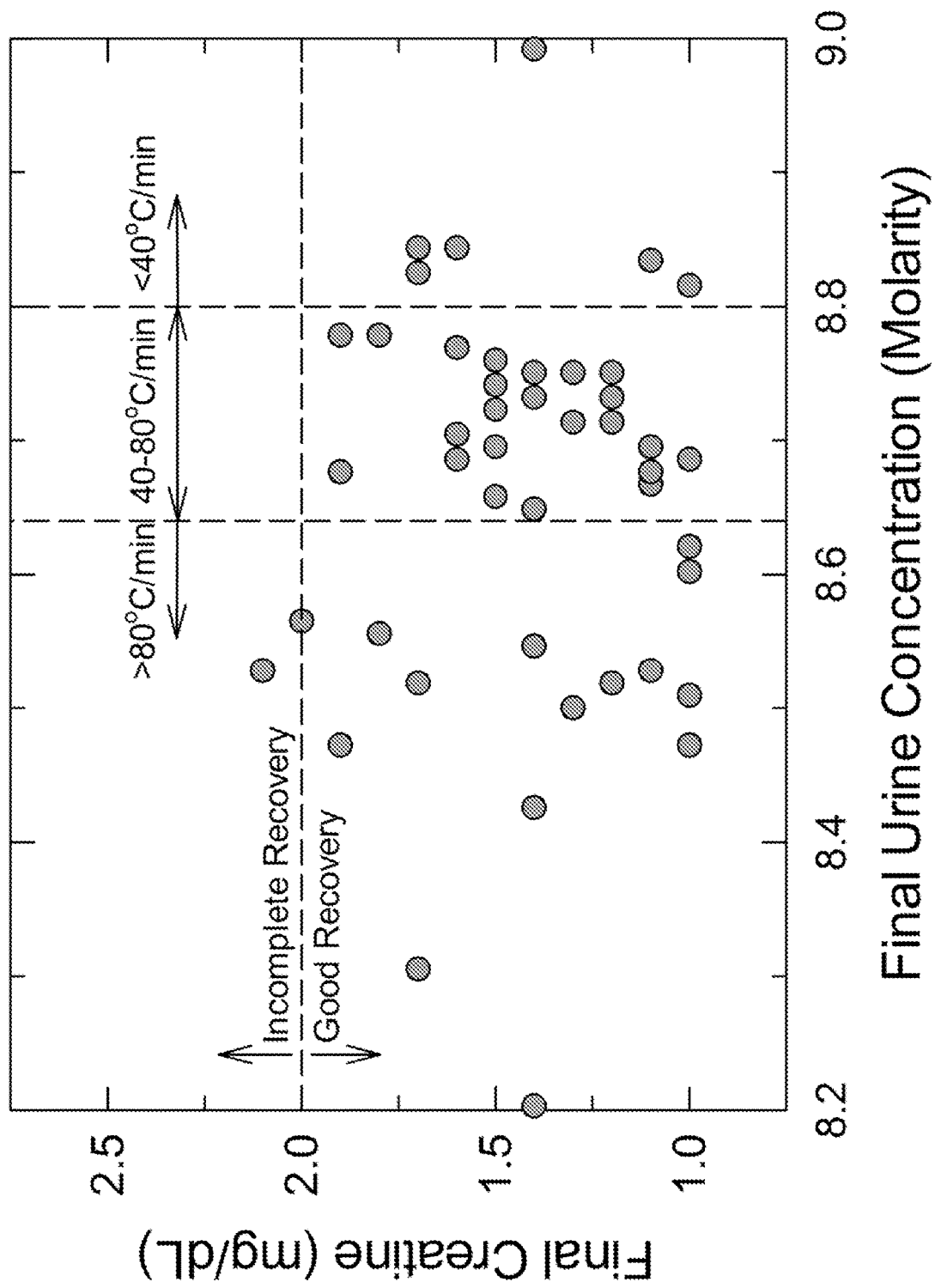
FIG. 6 demonstrates the viability of rabbit kidneys perfused according to the FlowLock method, wherein FlowLock methods were used that allowed in principle the kidney to escape from devitrification damage when warmed at achievable warming rates.

Example 5: The FlowLock Method Can Make Kidneys Immune to Devitrification While Preserving Their Viability after Transplantation FIG. 6 shows the final postoperative serum creatinine levels of many rabbits 14 days after they received kidneys that were perfused with M22 according to the FlowLock Method. These kidneys all achieved urine concentrations in the range of or above those that are permissive of vitrification without subsequent devitrification (ice formation upon rewarming above the glass transition temperature after previous vitrification). The graph plots final serum creatinine level against the urine concentration achieved at the end of the intended period of M22 perfusion, when the kidneys would have been removed from the perfusion apparatus and vitrified had vitrification been the object of the experiment. Instead, the object of the experiments shown was to evaluate the effect of renal equilibration with sufficient cryoprotectant to prevent devitrification had vitrification been attempted. As indicated in the figure, to reliably and consistently escape the formation of more than 1% w/w inner medullary ice during devitrification, kidneys with urinary concentrations below 8.64-8.65M at the end of M22 perfusion need to be warmed through the critical temperature zone for devitrification at a rate of greater than 80° C./min. Kidneys whose urine concentration is from 8.64 to 8.8M at the end of M22 perfusion can be reliably warmed with <1% w/w inner medullary ice from devitrification if the warming rate is from 40-80° C./min. The kidneys whose urine concentrations exceeded 8.8M at the end of M22 perfusion could in principle be vitrified and rewarmed at a warming rate of only 10-40° C./min and still escape forming more than 1% w/w inner medullary ice. However, as indicated by the return of serum creatinine levels to normal within two weeks in recipients of kidneys equilibrated to all three of these critical degrees of saturation with M22, the FlowLock method allows many kidneys to become immune to damaging degrees of ice formation and still recover fully after transplantation.

Therefore, the FlowLock Method represents a breakthrough over the previously known methods, and for the first time opens the door to the possibility of routine successful banking of kidneys by vitrification. It should also be noted that all rabbits received immediate contralateral nephrectomies, meaning that the M22-perfused kidney was the sole renal support from the day of its transplantation.

Also, as shown in FIG. 6, no clear trend was seen between the potential for full recovery of renal function (as measured by the serum creatinine level after 14 days of transplantation) and the final urine concentration of cryoprotectant. Furthermore, the same lack of a trend was found to apply when renal injury was measured by the peak creatinine level or by the overall probability of recipient survival within the different equilibration zones depicted. Remarkably, the mean peak serum creatinine level after transplanting kidneys in the zone from 8.64M-8.8M urine cryoprotectant was about 9.5 mg/dl, whereas the mean peak creatinine level for kidneys whose urine concentration exceeded 8.8M was 9 mg/dl, and the mean peak creatinine level of kidneys perfused with the previously known method at a constant pressure of 40 mmHg was also about 9 mg/dl (Fahy et al., 2004), despite the fact that the previously known method gives much lower urinary cryoprotectant concentrations, which are completely inadequate for vitrification. Thus, the FlowLock Method greatly improves renal protection against devitrification without itself causing injury, if practiced correctly, in contrast to all previously known methods.

There are currently a variety of newer electromagnetic warming methods that should be able to heat formerly vitrified rabbit kidneys and larger kidneys as well as other large organs at rates of at least 80-160° C./min over the temperature range of greatest susceptibility to devitrification. Therefore, the benchmark warming rates referred to in FIG. 6 are meaningful and achievable in practice.

Example 6: Setting Two Separate Values for the Upper Perfusion Pressure Limit

It is possible that in at least some cases, organs being warmed from −22° C. or especially from temperatures below −22° C. may require less powerful perfusion during the separate or combined rewarming/cryoprotectant dilution procedures described in the cited art. For that reason, it is contemplated that, for systems sensitive to higher perfusion pressures or flow rates during the said rewarming and/or concentration reduction steps, a second upper limit on arterial pressure, lower than the first, may be employed during those steps. It is anticipated that, typically, this second upper limit on arterial perfusion pressure should ideally be about halfway between the standard arterial perfusion pressure in the absence of cryoprotectant and the first upper limit on arterial perfusion pressure. For example, if the standard arterial perfusion pressure is 40 mmHg and the first upper limit on arterial perfusion pressure is 80 mmHg, the second upper limit on arterial perfusion pressure should be around 60 mmHg. Because systems will vary in their needs, the second upper limit on arterial perfusion pressure may be anywhere between the standard arterial perfusion pressure and the first upper limit on arterial perfusion pressure, but it is anticipated that the most advantageous range for the second upper limit on arterial perfusion pressure will be generally from the standard arterial perfusion pressure plus 20% of the difference between the standard arterial perfusion pressure and the first upper limit on arterial perfusion pressure to the standard arterial perfusion pressure plus 80% of the difference between the standard arterial perfusion pressure and the first upper limit on arterial perfusion pressure. Thus, if the standard pressure is 40 mmHg and the first upper pressure limit is 80 mmHg, the ideal range for a second upper pressure limit would be from (40+40×0.2) to (40+40×0.8)=48-72 mmHg.

There are two situations under which a second upper arterial perfusion pressure limit may apply. In the first, the system has been disconnected from the perfusion machine for cooling to below −22° C. and rewarming and is to be reperfused at the second upper arterial perfusion pressure. If the pressure prior to disconnecting the system from the perfusion machine was equal to or below the second upper arterial perfusion pressure, then the existence of a predetermined second upper arterial perfusion pressure is moot. In the second scenario, the arterial perfusion pressure exceeds the second upper arterial perfusion pressure. In both of the applicable scenarios, perfusing the system at the second upper arterial perfusion pressure requires that the arterial flow rate be lower than the set minimum arterial flow rate. Therefore, in both scenarios, the system is perfused at the second upper arterial perfusion pressure limit by adjusting flow to establish a pressure equivalent to this new upper pressure limit. As viscosity drops due to increased temperature and/or reduced arterial perfusate concentration, flow is increased to maintain the second upper arterial perfusion pressure limit until the flow equals the set minimum arterial flow, after which arterial flow is held constant until the pressure declines to the standard pre-cryoprotectant perfusion pressure. After this, flow is increased as necessary to maintain the latter standard pressure.

The methods of Example 6 may be useful particularly for organs such as the liver, which has a very tenuous and delicate vascular system, or the lung, which has a tendency to develop pulmonary edema at higher perfusion pressures. It may also be useful for biological systems that have been previously vitrified or otherwise cryopreserved, whose vascular systems may be more easily injured by higher perfusion pressures than non-vitrified or non-cryopreserved biological systems.

Example 7: Accelerated Washout Protocol

The final variation is for organs that can tolerate more prolonged exposure to higher perfusion pressures and to higher shear rates at the vascular wall during the removal of cryoprotectants. For these organs, cryoprotectant administration is carried out as described above, but when it is time to begin removing the cryoprotectant, a modified procedure is used. In this modified procedure, the arterial perfusion pressure that is present at the end of the cryoprotectant loading process is maintained for a time longer than the time required for the arterial flow rate to increase to equal or exceed the minimum set arterial flow rate, resulting in more rapid perfusion rates during cryoprotectant washout than in the other methods described above. As one possible, non-limiting example, in the protocol depicted in FIG. 2, the arterial pressure present at the end of the M22 plateau phase could be maintained until the end of the first post-M22 cryoprotectant plateau phase (i.e., for 10 min after beginning cryoprotectant washout), or until the end of the second post-M22 cryoprotectant plateau phase (i.e., for 20 min after beginning cryoprotectant washout), during which time arterial flow rates would increase substantially, rather than locking flow at the minimum set arterial flow rate until the arterial perfusion pressure declined to the standard arterial perfusion pressure. (In FIG. 2, Experiment 1, high pressures were maintained for about 10 min after the end of M22 perfusion because the arterial flow was below the set minimum flow until then, and the kidney survived in this and similar experiments. Example 7 extends this case to maintaining higher pressures even when the arterial flow exceeds the set minimum flow.) At the end of the extended high-pressure washout period, flow is then locked at the then-current rate until the arterial perfusion pressure declines to the standard arterial perfusion pressure, after which pressure is locked at the standard arterial perfusion pressure, and flow is allowed to increase as necessary to maintain that arterial perfusion pressure. The minimum beneficial duration of the extended high-pressure washout period will generally be 1 min or longer.

The method of Example 7 is based in part on the "pipeline" analogy described in Example 4. It has been observed (Fahy, unpublished observations) that when the M22 phase of a perfusion ends, urine concentrations of M22 solutes continue to rise for several minutes, even as arterial concentrations rapidly decline. Once again, the wave front of dilute cryoprotectant requires finite time to displace the more concentrated cryoprotectant previously delivered, including cryoprotectant more concentrated that could be observed during intentional M22 perfusion due to its failure to emerge from the nephrons in which it was still contained within the period of observation. It is speculated that one reason injury to the kidney does not depend on the urine concentration at the end of M22 perfusion is that injury is more dependent upon the concentration of M22 within the nephron several minutes after the formal M22 perfusion phase is completed, at which time nephron concentrations are reaching a peak, just before declining. On the basis of this reasoning, it would be advantageous to accelerate displacement of the high cryoprotectant concentrations within the nephron after the intended M22 perfusion period by maintaining a higher glomerular filtration rate as well as a higher vascular flow rate, thus accelerating the rate of "urine" flow.

A second beneficial effect of the method of Example 7 is that by locking flow at a higher rate, the arterial perfusion pressure is expected to decline to the standard arterial perfusion pressure at a lower (gentler) rate after the flow rate is locked than in the other variations of the FlowLock washout method.

Example 8: Metes and Bounds of the FlowLock Method

Ranges of valuable flow rates for biological systems to be cryoprotected or vitrified depend on the system in question. For example, in Example 1, global flows on the order of 0.04-0.05 (ml/min)/g (about 50% of the pre-cryoprotectant flow rate) were appropriate and sufficient for 80% of the tissues and organs sampled, whereas in Example 2, involving the more rapidly-flowing kidney, flows ranging from about 0.1-0.3 (ml/min)/g (about 10-30% of the pre-cryoprotectant flow rate) were found to be most efficacious. Minimum locked flows of up to just under 0.5 (ml/min)/g (about 50% of the pre-cryoprotectant flow rate in that specific case) were found to be compatible with full recovery of perfused rabbit kidneys, but with more transient damage and a possibly lower survival rate. Based on these results, the range of flow rates applicable to the locked flow stages of the FlowLock Method should be limited to about 0.04-0.5 (ml/min)/g, or for greater safety, to about 0.04-0.4 (ml/min)/g, or to about 10%-50% of the flow rate that is normal when viscosity is normal (i.e., when there is no cryoprotectant present), especially when the tissue or organ is to be perfused with a solution having a viscosity in the range of 4-5 cP at room temperature or 30-45 cP between −20 and −24° C. For considerably less viscous solutions, having viscosities from about 1.2-2 cP at room temperature, locked flows can be higher, such as up to 0.1 (ml/min)/g for whole organisms and up to 0.6-0.8 (ml/min)'g for high flow organs such as the kidney or, in general, about 50%-100% of pre-cryoprotectant flow rates. Upper flow limits between these two viscosity regimes should be scaled based on viscosity and vascular resistance so as to keep pressures within the limits specified below.

Ranges of valuable upper pressure limits for the FlowLock method depend on the system to be cryoprotected or vitrified, different systems having different tolerance to high pressures under different experimental conditions. Organs such as the liver, which are normally perfused at portal vein pressures near 5 mmHg, or the lung, whose pulmonary artery pressure must normally be kept at 8 mmHg or below to avoid pulmonary edema, need to be handled differently from organs like the kidney, which can tolerate 80-90 mmHg or above. Therefore, in general, the FlowLock Method should not generate pressures during the perfusion of peak concentrations of cryoprotectant that exceed the in vivo pressures or pressure limits that are normally experienced in vivo by the organ or organ system at hand. These normal pressures are well known to those of skill in the art. In addition, the FlowLock Method generates pressures that depend not only on the locked flow, but also on the viscosity of the perfusate. Based on this, the limiting pressures are desirably less than pressures normally experienced by the given organ or organ system in vivo when lower-viscosity perfusates are to be used. In general, peak arterial pressures of 80-130 mmHg and below are preferred for most organs, including the kidney and the heart, peak pressures of 50-90 mmHg are preferred for the non-fixed brain, and peak arterial pressures of 5-15, or more preferably 5-10 mmHg are preferred for the liver and the lung. As illustrated in FIG. 2, although upper limits may be set, lower pressures are of course acceptable and even more preferred in cases in which they enable sufficiently rapid and complete cryoprotectant equilibration to be achieved in the process of interest. There is no requirement that an upper pressure limit actually be encountered.

In general, one wishes to use the maximum flows that are found to be acceptable for the perfused biological system at hand and are found not to generate pressures above those that are acceptable for that system (the upper pressure limits). Empirically, one of skill in the art will always be able to determine suitable pressure limits for the viability or physical integrity of a specific system in a small number of experiments, given the guidance provided by the present specification.

The duration of perfusion with cryoprotectants will also depend on the biological system being preserved. On the basis of current information, perfusion at the peak concentration for as long as 30-60 min may be required in some cases, whereas in other cases shorter perfusion times will be sufficient. In general perfusion times at peak concentration are expected to be within the range of 10-60 min for optimal results, and the most ideal range is expected to be from 10-30 min for most systems.

The duration of prolonged maintenance of peak arterial perfusion pressure after the onset of cryoprotectant washout in the method of Example 7 should generally be from 1-30 min, or more commonly, 1-20 min.

Because the invention is a process that depends on viscosity, relative flow rates, and limiting pressures, and not on how viscosity is changed (i.e., not on the interaction between specific cryoprotectant formulation concentrations and temperature, and not on the use of any particular cryoprotectant solution or solutions), there are no specific metes and bounds on cryoprotectant concentration or perfusion temperatures. For example, poly-acetylated trehalose may be very viscous in very low concentrations compared to other pCPA, and even at much higher temperatures than described in FIG. 2, for example, even at room temperature, but all that matters for the successful practice of the disclosure is that flow and pressure and their interplay stay within the process limits described herein and that temperature stays within the range that is compatible with life and that is warm enough to permit perfusion to continue (i.e., 37° C. to −40° C.). Nevertheless, it is anticipated that the FlowLock Method will be of greatest utility when applied to the perfusion of "ordinary" pCPA (pCPA <100 Da in molecular mass) in the range of 4-11M.

Cited publications/Patents, all of which are incorporated herein by reference in their entireties:

Fahy, G. M., Wowk, B., Wu, J., Phan, J., and Zendejas, E. Cryopreservation of organs by vitrification: perspectives and recent advances. Cryobiology 48: 157-178, 2004.

Fahy, G. M., Wowk, B., Pagotan, R., Chang, A., Phan, J., Thomson, B., and Phan, L. Physical and biological aspects of renal vitrification. Organogenesis 5: 167-175, 2009 (open source publication: www.landesbioscience.com/journals/organogenesis/article/9974).

U.S. Pat. No. 8,679,735 B2: Methods and compositions for the cryopreservation of organs. (Nov. 6, 2013), G. M. Fahy and B. Wowk.

US Patent Publication U.S. Pat. No. 5,338,662 A: Organ perfusion device (lapsed), Fereydoon Sadri Karow, A. M., Jr. Cryoprotectants—a new class of drugs. J. Pharm. Pharmacol. 21: 209-223, 1969.

Abazari, A., Meimetis, L. G., Budin, G., Bale, S. S., Weissleder, R., and Toner, M. Engineered trehalose permeable to mammalian cells. PLOS One 10: e0130323, 2015.

I claim:

1. A method for perfusing tissues, organs, organ systems, or vascularized organisms with cryoprotective agents by a perfusion process comprising:
    a) setting a lower arterial flow rate limit for the perfusion process;
    b) increasing the concentration of cryoprotective agents in an arterial perfusate at a constant first arterial perfusion pressure until the rising viscosity of said perfusate causes the arterial flow rate to decline to become equal to the said set lower arterial flow rate limit of step a);
    c) holding the arterial flow rate constant at the set lower arterial flow rate limit of step a);
    d) allowing the arterial perfusion pressure to rise from the first arterial perfusion pressure of step b) to a higher pressure equal to or below a preset maximum arterial perfusion pressure as a result of rising perfusate viscosity in combination with the constant lower arterial flow rate limit of steps a) and c); and then
    e) either:
        i. continuing to perfuse the tissue, organ, organ system, or vascularized organism at the set lower arterial flow rate limit of step a) above, if the arterial perfusion pressure does not reach the preset maximum arterial perfusion pressure of step d) above, or,
        ii. if the arterial perfusion pressure reaches the preset maximum arterial perfusion pressure of step d) above, reducing said arterial flow rate to below the set lower arterial flow rate limit of step a) above so as to maintain the arterial perfusion pressure at the preset maximum arterial perfusion pressure of step d).

2. The method of claim 1, further comprising, after all of the steps of claim 1:
    f) reducing the viscosity of the arterial perfusate by beginning to raise the temperature of the arterial perfusate or by lowering the concentration of cryoprotectant in the arterial perfusate, or both, while continuing perfusion, and then;
    g) if the arterial perfusion pressure is below the preset maximum value of step d) of claim 1, continuing to perfuse at the set lower arterial flow rate limit of step a) of claim 1 until the viscosity reduction of step f) causes arterial pressure to fall to the first arterial perfusion pressure of step b) of claim 1, and thereafter maintaining the arterial perfusion pressure at the first arterial perfusion pressure of step b) of claim 1 by increasing the arterial flow rate so as to do this; or
    h) if the arterial perfusion pressure is equal to the preset maximum arterial perfusion pressure of step d) of claim 1 and the arterial flow rate is lower than the set lower arterial flow rate limit of step a), increasing arterial flow rate so as to maintain this pressure as perfusate viscosity falls according to step f) above until such time as the arterial flow rate becomes equal to the set lower limit of arterial flow rate of step a) of claim 1 and then holding the arterial flow rate constant at the set lower arterial flow rate limit of step a) of claim 1 until the arterial perfusion pressure falls to become equal to the first arterial perfusion pressure of step b) of claim 1, and thereafter maintaining the arterial perfusion pressure at the first arterial perfusion pressure of step b) of claim 1 by increasing the arterial flow rate so as to do this.

3. The method of claim 1, further comprising, after all of the steps of claim 1:
    f) reducing the viscosity of the arterial perfusate by beginning to raise the temperature of the arterial perfusate or by lowering the concentration of cryoprotectant in the arterial perfusate, or both, while perfusing the biological system, and then
    g) if the arterial perfusion pressure at the end of step e) of claim 1 is higher than a predetermined second maximum arterial perfusion pressure lower than the preset maximum perfusion pressure of step d) of claim 1 but higher than the first arterial perfusion pressure of step b) of claim 1, then adjusting arterial flow rate to establish the said predetermined second maximum arterial perfusion pressure, provided that said arterial flow rate sufficient to establish the said predetermined second maximum arterial perfusion pressure does not exceed the set lower arterial flow rate limit of step a) of claim 1;
    h) as the viscosity of the arterial perfusate is lowered by beginning to raise the temperature of the arterial perfusate or by lowering the concentration of cryoprotectant in the arterial perfusate, or both, while continuing perfusion, increasing the arterial flow rate so as to maintain the arterial perfusion pressure at the predetermined second maximum arterial perfusion pressure of step g);
    i) holding the arterial flow rate constant when the arterial flow rate becomes equal to the pre-set lower arterial flow rate limit of step a) of claim 1, until the arterial perfusion pressure becomes equal to the first arterial perfusion pressure of step b) of claim 1; and then j) raising the arterial perfusion pressure as needed to maintain the first arterial perfusion pressure of step b) of claim 1.

4. The method of claim 1, further comprising, after all of the steps of claim 1:
    f) reducing the viscosity of the arterial perfusate by beginning to raise the temperature of the arterial perfusate or by lowering the concentration of cryoprotectant in the arterial perfusate, or both, while continuing perfusion, and at the same time
    g) maintaining the arterial perfusion pressure that is present at the end of step e) of claim 1 for a time longer than the time required for the arterial flow rate to increase to equal or exceed the minimum set lower arterial flow rate limit of step a) of claim 1; and then
    h) locking arterial flow rate at the rate present at the end of the said time longer than the time required for the arterial flow rate to increase to equal or exceed the lower arterial flow rate limit of step a) of claim 1 until the arterial perfusion pressure declines to the first arterial perfusion pressure of step b) of claim 1; and then i) locking the arterial pressure at the first arterial perfusion pressure of step b) of claim 1 by increasing the arterial flow rate so as to maintain that arterial perfusion pressure.

\* \* \* \* \*